United States Patent [19]

Bachman et al.

[11] 3,933,781

[45] Jan. 20, 1976

[54] PROCESS FOR THE PREPARATION OF α-L-ASPARTYL-L-PHENYLALANINE ALKYL ESTERS

[75] Inventors: Gerald L. Bachman; Marvin L. Oftedahl; Billy D. Vineyard, all of St. Louis, Mo.

[73] Assignee: Monsanto Company, St. Louis, Mo.

[22] Filed: Nov. 5, 1973

[21] Appl. No.: 412,928

[52] U.S. Cl. .............................................. 260/112.5
[51] Int. Cl.² .................... C07C 103/52; A23L 1/22
[58] Field of Search .................................. 260/112.5

[56] References Cited
UNITED STATES PATENTS

| | | | |
|---|---|---|---|
| 3,769,333 | 10/1973 | Lapidus et al. | 260/112.5 |
| 3,798,204 | 3/1974 | Nakajima et al. | 260/112.5 |
| 3,798,206 | 3/1974 | Uchiyama et al. | 260/112.5 |

FOREIGN PATENTS OR APPLICATIONS

| | | | |
|---|---|---|---|
| 2,040,473 | 1/1971 | France | 260/112.5 |

OTHER PUBLICATIONS

Mazur et al.: J. Am. Chem. Soc., 91, 2684–2691 (1969).
E. Schroder and K. Lubke, "The Peptides," Vol. I, pp. 52–53, Academic Press, New York (1965).
King et al.: J. Chem. Soc., 1949, 3315–3319.
Bodanszky and Ondetti, "Peptide Synthesis," Interscience, New York, 1966, p. 97.

*Primary Examiner*—Joseph P. Brust
*Assistant Examiner*—Reginald J. Suyat
*Attorney, Agent, or Firm*—Howard C. Stanley; J. E. Maurer; Neal E. Willis

[57] ABSTRACT

A process for the preparation of α-L-aspartyl-L-phenylalanine alkyl esters wherein L-phenylalanine is reacted with N-protected-L-aspartic anhydride, the resulting product is treated to yield α-L-aspartyl-L-phenylalanine which is esterified with an alkanol to yield an α-L-aspartyl-L-phenylalanine alkyl ester which is recovered.

Novel precursors for α-L-aspartyl-L-phenylalanine alkyl esters are prepared in the process of this invention.

14 Claims, No Drawings

PROCESS FOR THE PREPARATION OF α-L-ASPARTYL-L-PHENYLALANINE ALKYL ESTERS

This invention relates to a process for the preparation of α-L-aspartyl-L-phenylalanine alkyl esters. α-L-aspartyl-L-phenylalanine alkyl esters, particularly the methyl ester, are well known for their usefulness as sweetening agents.

α-L-aspartyl-L-phenylalanine alkyl esters have been produced by a chemical synthesis route that heretofore involved the use of L-phenylalanine alkyl esters as reactants. These methods of production of α-L-aspartyl-L-phenylalanine alkyl esters have been found to be excessively complicated and expensive resulting in high production costs.

It is the primary object of this invention to provide a novel synthetic process for the preparation of α-L-aspartyl-L-phenylalanine alkyl esters.

It is a still further object of this invention to provide novel precursor compounds for the preparation of α-L-aspartyl-L-phenylalanine alkyl esters.

Further objects, aspects and advantages of this invention will be apparent from the description which follows.

According to the present invention, there is provided a process for preparing α-L-aspartyl-L-phenylalanine alkyl esters which comprises reacting N-protected-L-aspartic anhydride with L-phenylalanine to form N-protected- α-L-aspartyl-L-phenylalanine, removing the protecting group from the N-protected-α-L-aspartyl-L-phenylalanine to form α-L-aspartyl-L-phenylalanine and esterifying the α-L-aspartyl-L-phenylalanine with an alkanol to form an α-L-aspartyl-L-phenylalanine alkyl ester which is recovered. Novel compounds which are useful in the process of the present invention are the N-protected- α-L-aspartyl-L-phenylalanines.

Synthesis of α-L-aspartyl-L-phenylalanine alkyl esters, according to this invention, can proceed in the following general sequence of reactions:

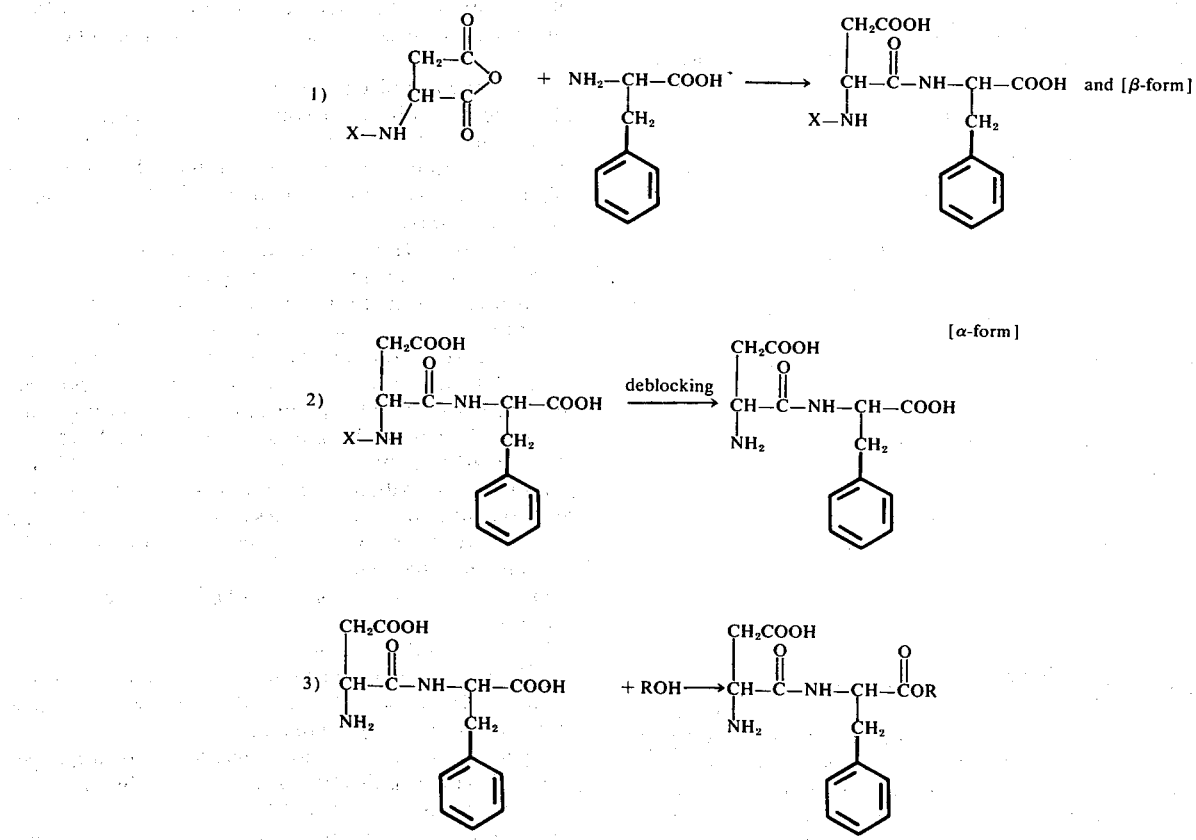

In the above equations X represents an amino protecting group and R represents a lower alkyl having from 1 to 3 carbon atoms.

As shown in equation 1) the starting reactants are an N-protected-L-aspartic anhydride and L-phenylalanine which are reacted to form N-protected- α-L-aspartyl-L-phenylalanine. The amino protecting group can be any of those known to persons skilled in the art as exemplified by formyl, acetyl, benzoyl, substituted and unsubstituted carbobenzoxy, t-butoxycarbonyl and the hydrohalide salt. Particularly preferred is N-formyl-L-aspartic anhydride which can be prepared, for instance, as shown in French Pat. No. 2,040,473 wherein N-formyl-L-aspartic acid is treated with acetic anhydride in an organic solvent at 0°–60°C.

The L-phenylalanine is readily available by known synthetic and/or fermentation processes and is usually employed in amounts of from 2.0 to 0.5 moles per mole of N-protected-L-aspartic anhydride, preferably about 1,0 mole of L-phenylalanine per mole of N-protected-L-aspartic anhydride. Any solvent can be used, provided that the reactants are soluble in, and do not unduly react with, the solvent. Examples of suitable solvents are ethyl acetate, methyl propionate, tetrahydrofuran, dioxane, ether, chloroform, toluene and acetic acid. Glacial acetic acid is particularly preferred.

Although the reaction proceeds smoothly at room temperature, the reaction rate can be increased by heating the reaction mixture. However, if the reaction temperature is too high secondary reactions, such as racemization, tend to occur. Therefore, the reaction is preferably carried out at a temperature of below about 80°C., preferably at a temperature of below about 60°C.

The reaction mass obtained from the reaction illustrated in equation 1) will contain the desired product

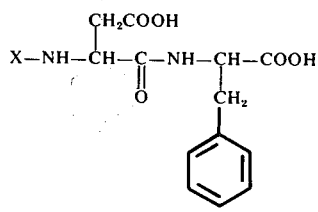

(hereinafter referred to as the "α-form") and an undesired by-product

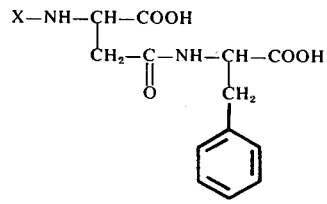

(hereinafter referred to as the "β-form").

Surprisingly, the α-form and β-form reaction products are usually formed in a ratio of from about 4 parts α-form to about 1 part β-form when the reaction is carried out in glacial acetic acid at a reaction temperature of from about 20°C. to about 60°C. It has been found that relatively pure α-form can then be recovered from the reaction mass by crystallization. This is a particularly advantageous feature of the instant invention. The α-form thus recovered can be further subjected to the second step of the instant invention. The β-form, which remains in the resulting mother liquor solution can be subjected to further treatment, such as hydrolysis, to recover L-aspartic acid and L-phenylalanine for recycle to earlier stages.

Alternatively, the reaction mass containing both reaction products can be carried forward in the next reaction sequence.

The resulting N-protected- α-L-aspartyl-L-phenylalanine is then treated (equation 2) to remove the protecting group to obtain α-L-aspartyl-L-phenylalanine. Any method suitable for removing protecting groups from amines is appropriate. Examples of such methods are catalytic hydrogenation and treatment with mineral acids or bases. It is preferred to remove the protecting group, particularly the formyl group, by acid hydrolysis. This hydrolysis can be carried out in, for instance, a dilute aqueous hydrochloric acid solution. The conversion to α-L-aspartyl-L-phenylalanine is surprisingly very high, i.e., on the order of 95% or higher based on the N-protected- α-L-aspartyl-l-phenylalanine so treated. Another medium for such treatment is an acetic acid-hydrochloric acid aqueous solution.

α-L-aspartyl-L-phenylalanine can then be recovered by precipitation and liquid/solid separation. Such precipitation can, for instance, be produced by pH adjustment when the protecting group has been removed in an acid solution. The major undesired by-product remaining in the mother liquor is β-L-aspartyl-L-phenylalanine, if its precursor is carried forward as suggested above, which can be treated, such as by hydrolysis, to recover L-aspartic acid and L-phenylalanine for recycle to earlier stages.

As illustrated in equation 3), α-L-aspartyl-L-phenylalanine is then subjected to esterification with an alkanol to form an α-L-aspartyl-L-phenylalanine alkyl ester.

The solvent utilized in this reaction can be any suitable organic solvent provided that the reactants are soluble in such solvent and do not interfere with the desired reaction. Examples of suitable solvents are the alkanol, tetrahydrofuran, methylene chloride, chloroform and benzene. The alkanol is particularly preferred. It is preferred that the reaction be carried out with as little water present as possible.

It is preferred that this esterification reaction be carried out in an acidic media. For instance, the reaction can be carried out in alkanol which contains from about 1 to about 10 moles of hydrogen chloride per mole of α-L-aspartyl-L-phenylalanine, preferably from about 1.05 to about 2.0 moles of hydrogen chloride per mole of α-L-aspantyl-L-phenylalanine. It is readily apparent to one skilled in the art that the esterification reaction may, in fact, be between an acid salt of the α-L-aspartyl-L-phenylalanine and the alkanol but for convenience this reaction will be referred to herein as being between α-L-aspartyl-L-phenylalanine and the alkanol.

The temperatures utilized should be from about −20°C. up to about the boiling point of the reaction mass with from about 20°C. to 40°C. being particularly preferred when using methanol.

In general the molar ratio of alkanol to α-L-aspartyl-L-phenylalanine utilized should be from about 0.5 to about 50, preferably 1.0 to 10.

Inherent in this esterification reaction is the formation of the following undesired by-products:

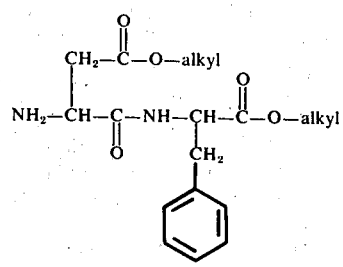

(hereinafter referred to as the "diester") and

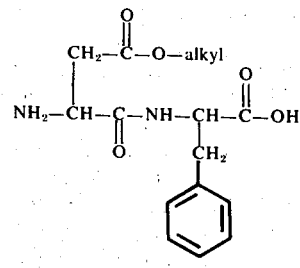

(hereinafter referred to as the "aspartyl ester").

In addition to these two undesired by-products, the reaction mass will also contain unreacted α-L-aspartyl-L-phenylalanine. Reactions leading to the desired product and by-products are all equilibrium reactions. It has been discovered that the reactions provide a large formation of α-L-aspartyl-L-phenylalanine alkyl ester by carrying out the esterification for purposes of illustration, in methanol in the presence of in excess of one mole of hydrogen chloride per mole of α-L-aspartyl-L-phenylalanine normally about 1.1 moles of hydrogen chloride per mole of α-L-aspartyl-L-phenylalanine. At about room temperature as much as about 40 to 45 percent of the α-L-aspartyl-L-phenylalanine is converted to α-L-aspartyl-L-phenylalanine methyl ester.

The α-L-aspartyl-L-phenylalanine alkyl ester can then be recovered. For instance, by subjecting the resulting reaction mass to partial neutralization to precipitate unreacted α-L-aspartyl-L-phenylalanine which can then be recovered by solid/liquid separation procedures. The remaining solution can then be treated, as by distillation to remove unreacted alkanol. The residual reaction mass can then be treated to recover the desired product. For instance, by treatment with a hydrochloric acid solution causing the precipitation of the hydrochloride salt of α-L-aspartyl-L-phenylalanine alkyl ester. The hydrochloride salt can then be recovered and converted to the desired product.

It has surprisingly been found that the hydrochloride salt of α-L-aspartyl-L-phenylalanine alkyl ester is significantly less soluble when compared to the other above-named compounds and can therefore be easily separated and recovered by solid/liquid separation in that form. Essentially all of the other compounds remain in the mother liquor and can be hydrolyzed to α-L-aspartyl-L-phenylalanine which can be recovered and/or recycled to the esterification reaction.

The following examples are given to illustrate the instant invention in detail. It is to be understood that the specific details given in the examples are not to be construed as limiting the scope of the invention.

The materials and procedures utilized in the thin layer chromatography (TLC) analyses in the examples are as follows:

A. Plate
Silica Gel F on glass plate supplied by Brinkman Instrument Inc., Westbury, N. Y. 11590.
B. Solvent systems

| 1. | chloroform | 64% | (by volume) |
|---|---|---|---|
|  | methanol | 30% | " |
|  | acetic acid | 2% | " |
|  | distilled water | 4% | " |
| 2. | n-propanol | 70% | " |
|  | distilled water | 10% | " |
|  | methanol | 10% | " |
|  | formic acid | 10% | " |

C. Detection Spray Solutions
1. 0.3 g. of ninhydrin dissolved in a mixture of 100 ml. of n-butanol and 3 ml. of glacial acetic acid.
2. 1 g. of potassium iodide and 1 g. of soluble starch dissolved in 100 ml. of distilled water.
D. Procedures
After spotting and development in the appropriate solvent system the plate was air dried for 30 min. Ninhydrin spray — The plate was sprayed and held in a 100°C. oven for 15 min.
Starch-iodide spray — The place was placed in a chamber saturated with t-butyl hypochlorite vapor for 15 minutes, air dried for 30 minutes then sprayed with freshly prepared starch-iodide solution.

EXAMPLE 1

N-Formyl-α-L-Aspartyl-L-Phenylalanine

Into a suitable reaction vessel at 45°–50°C., 34.6 g. (0.21 mole) of L-phenylalanine is added in about 45 minutes to a mixture of 30 g. (0.21 mole) of N-formyl-L-aspartic anhydride and 300 g. of glacial acetic acid. The resulting mixture is held for an additional 30 minutes, then cooled to 25°C. The resulting crystalline product is collected by filtration and washed with 50 g. of glacial acetic acid. The yield of N-formyl-α-L-aspartyl-L-phenylalanine is 40.5 g., m.p. 180°–182°C. TLC analysis of this product indicates no detectable β-form contamination.

EXAMPLE 2

To a suitable reaction vessel is added 288 g. (2.82 mole) of acetic anhydride to 428 g. of 97% formic acid over a period of about 45 minutes at 25°C., and held for an additional 45 minutes. 147 g. (1.1 mole) of L-aspartic acid is charged to the reaction vessel. The resulting solution is stirred for about 3.5 hours at 25°C. Any excess formic acid is removed by fractional distillation. Sufficient glacial acetic acid is added so as to have a total of 972 g. of acetic acid present. At 50°C. 174 g. (1.05 mole) of L-phenylalanine is added with a screw feeder in 45 minutes. The resulting mass is held at 50°C. for 30 minutes, then allowed to cool to 25°C. The crystalline N-formyl-α-L-aspartyl-L-phenylalanine is collected on a centrifuge and washed with 200 cc. of glacial acetic acid. Final dry weight of the product is 178 g., m.p. 182°–184°C. Thin layer chromatography indicated substantially pure N-formyl-α-L-aspartyl-L-phenylalanine with no detectable β-form present.

EXAMPLE 3

α-L-Aspartyl-L-Phenylalanine

A mixture of 100 g. (0.322 mole) of N-formyl-α-L-aspartyl-L-phenylalanine and 59.7 g. of 37% HCl (0.607 mole) in 392 cc. of water is heated at 60°C. for 4–5 hours. The resulting solution is partially neutralized with 32.6 g. (0.41 mole) of 50% NaOH, then cooled to 20°–25°C. The solid product formed was collected and washed with 50 cc. of cold water (5°C.). The amount of α-L-aspartyl-L-phenylalanine recovered, first crop, is 32.7 g.

The combined mother liquor and water wash from the first crop is further neutralized at 60°C. with 17.6 g. (0.22 mole) of 50% NaOH. Cooling the reaction mass to 25°C., and collecting the solid formed and washing with 50 cc. of cold water yields another 45 g. of α-L-aspartyl-L-phenylalanine. Total yield of α-L-aspartyl-L-phenylalanine is 77.7 g., $[\alpha]_D^{20}$ + 30.2°, C=0.7, 75% aqueous acetic acid.

EXAMPLE 4

α-L-Aspartyl-L-Phenylalanine

To 441 g. of 97% formic acid in a 2 liter flask, equipped with stirrer, was added dropwise over 95 minutes 286 g. (2.8 mole) of acetic anhydride. After addition was complete, the solution was stirred 45 minutes at ambient temperature. To this solution was added 147 g. (1.1 mole) of L-aspartic acid in one portion and stirring was continued at ambient temperature for 3.5 hours. Excess formic acid was removed by fractional distillation at 30 to 60 mm. of vacuum. Acetic acid (244 g.) was added to the pot residue so as to have a total of 379 g. of acetic acid present.

To this solution of N-formyl-L-aspartic anhydride, at 50°C., was added portionwise over 1 hour 174 g. (1.05 mole) of L-phenylalanine. The reaction mass was stirred at 50°C. for 1.5 hour.

The resulting reaction mass, containing both the α and β-form, was treated with 875 ml. of water and 195 g. of 37% hydrochloric acid and heated for 4 hours at 60°C. The product was precipitated from the foregoing hydrolysis solution by addition of 235.6 g. of 50% sodium hydroxide solution. The solids were separated by centrifugation and washed with 150 ml. of water. The cake was dried to yield 146.4 g. of product which was shown by thin layer chromatography to be α-L-aspartyl-L-phenylalanine with a purity greater than 95%; $[\alpha]_D^{20} + 27.7$, C=0.9, 75% aqueous acetic acid.

EXAMPLE 5

α-L-Aspartyl-L-Phenylalanine

To a 50°C. slurry of 6.0 g. (0.042 mole) of N-formyl-L-aspartic anhydride in 15.1 g. of acetic acid was added portionwise over 45 minutes, 6.92 g. (0.042 mole) of L-phenylalanine. After addition was complete the mixture was stirred 30 minutes.

This reaction mass, containing both α and β-forms, was treated with 35 ml. of water and 7.8 g. of 37% hydrochloric acid and stirred 4 hours at 60°C. The product was precipitated from the hydrolysis solution by addition of 8.1 g. of 50% sodium hydroxide solution. The solids were separated by filtration and washed with 5 ml. of water. The cake was dried to yield 7.1 g. of product which was shown by thin layer chromatography to be α-L-aspartyl-L-phenylalanine $[\alpha]_D^{20} + 29.5$, C=.8, 75% aqueous acetic acid.

EXAMPLE 6

0.825 g. (5 mmole) of L-phenylalanine was dissolved in 20 ml. of water containing 0.5 g. (5 mmole) of triethylamine and the resulting solution was cooled in an icebath. 0.83 g. (5.5 mmole) of L-aspartic anhydride hydrochloride was added to the cooled, stirred solution over a period of five minutes. The anhydride dissolved instantly. The solution was stirred at 5°C. for two hours, then allowed to warm to ambient temperatures with stirring.

Analysis of the reaction mixture by thin layer chromatography indicated that the mixture contained approximately 20% α-L-aspartyl-L-phenylalanine.

EXAMPLE 7

A solution of 46 mg. (0.16 mmole) of α-L-aspartyl-L-phenylalanine, 35 mg. (0.18 mmole) of p-toluene sulfonic acid monohydrate and 0.5 ml. of anhydrous methanol was maintained at reflux temperature (64.7°C.) for 1.5 hours. The resulting yields, based on the initial charge of α-L-aspartyl-L-phenylalanine, are as follows (by TLC):

| Product | % |
| --- | --- |
| α-L-aspartyl-L-phenylalanine methyl ester | 35–40 |
| α-L-aspartyl-L-phenylalanine (unreacted) | 15–20 |
| Aspartyl ester | 15–20 |
| Diester | 10–15 |

EXAMPLE 8

A solution of 46 mg. (0.16 mmole) of α-L-aspartyl-L-phenylalanine, 1.1 ml. of 0.37 N $H_2SO_4$—$CH_3OH$ solution (contains 0.2 mmole of $H_2SO_4$) and 4 ml. of anhydrous methanol was maintained at reflux (64.7°C.) for 1.5 hours. The resulting yields, based on the initial charge of α-L-aspartyl-L-phenylalanine, are as follows (by TLC):

| Product | % |
| --- | --- |
| α-L-aspartyl-L-phenylalanine methyl ester | 15–20 |
| α-L-aspartyl-L-phenylalanine (unreacted) | 35 |
| Aspartyl ester | 10 |
| Diester | trace |

EXAMPLE 9

A solution of 46 mg. (0.16 mmole) of α-L-aspartyl-L-phenylalanine, 0.43 mmole of pyrophosphoric acid and 5 ml. of anhydrous methanol was maintained at reflux (64.7°C.) for 3 hours. The resulting yields, based on the initial charge of α-L-aspartyl-L-phenylalanine, are as follows (by TLC):

| Product | % |
| --- | --- |
| α-L-aspartyl-L-phenylalanine methyl ester | 20–25 |
| α-L-aspartyl-L-phenylalanine (unreacted) | 35 |
| Aspartyl ester | 20–25 |
| Diester | 5–10 |

EXAMPLE 10

α-L-Aspartyl-L-Phenylalanine Methyl Ester

A solution of 1.86 g. of α-L-aspartyl-L-phenylalanine, 2.9 ml. of 2.6 N hydrochloric acid in methanol and 7.2 ml. of methanol was stirred at 30°C. for 2 hours. The resulting yields, based on the initial charge of α-L-aspartyl-L-phenylalanine, are as follows (by TLC):

| Product | % |
| --- | --- |
| α-L-aspartyl-L-phenylalanine methyl ester | 40–45 |
| α-L-aspartyl-L-phenylalanine (unreacted) | 20–25 |
| Aspartyl ester | 15–20 |
| Diester | 15–20 |

EXAMPLE 11

Into a suitable reaction vessel, equipped with thermometer, stirrer and condenser charge 111.5 g. (0.4 mole) of α-L-aspartyl-L-phenylalanine. Add 500 ml. of $CH_3OH$ and 132.5 ml. of 3.42 N HCl in methanol. Stir and heat to 30°C. for 2 hours. Cool to 25°C. and add 9.5 ml. (0.12 mole) of 50% NaOH over 15 minutes. Stir in an icebath for 1 hour and filter unreacted α-L-aspartyl-L-phenylalanine. Wash the α-L-aspartyl-L-phenylalanine cake with two 50 ml. portions of ice cold methanol. Dry the cake in a vacuum oven. 25 g. of α-L-aspartyl-L-phenylalanine (ca 90% pure) are recovered.

575 ml. of methanol is removed from the filtrate by distillation. 225 ml. of water and 41.5 ml. of 37% HCl (0.49 mole) is then added followed by stirring for 2 hours at 0°–5°C. Filter the solid hydrochloride salt of α-L-aspartyl-L-phenylalanine methyl ester and redissolve in 610 ml. of 50°C. water. With 17.45 g. (0.22 mole) of 50% NaOH adjust the pH of the resulting solution to 4–4.5 and stir for 2 hours at 5°C. Filter the α-L-aspartyl-L-phenylalanine methyl ester and wash with five 30 ml. portions of 0°–5°C. water. Dry the α-L-aspartyl-L-phenylalanine methyl ester in vacuum oven. The yield is 33.65 g. with a greater than 98% purity (by TLC).

EXAMPLE 12

α-L-Aspartyl-L-Phenylalanine Methyl Ester

A solution of 22.3 g. of α-L-aspartyl-L-phenylalanine, 24.3 ml. of 3.76 N hydrochloric acid in methanol and 25 ml. of methanol was stirred at 30°C. for 1.5 hours. After the esterification reaction was completed, 2.85 g. of 50% sodium hydroxide solution was added dropwise over a 12 min. period to precipitate the unreacted α-L-aspartyl-L-phenylalanine. The reaction mass was stirred 45 minutes at ambient temperature. The crystalline α-L-aspartyl-L-phenylalanine was removed by filtration. The α-L-aspartyl-L-phenylalanine cake was washed with two 10 ml. portions of methanol and dried to yield 6.5 g. of α-L-aspartyl-L-phenylalanine (ca 90% pure by TLC).

The filtrate and washings were returned to the reaction vessel and the methanol was removed by vacuum distillation. To the residue after distillation was added 45 ml. of water and 8.3 ml. of 37% hydrochloric acid. The reaction mass was stirred at 0°–5°C. for 1.5 hours, and the solid hydrochloride salt of α-L-aspartyl-L-phenylalanine methyl ester was recovered by filtration.

The recovered cake was dissolved in 120 ml. of 50°C. water and the pH of the resulting solution was adjusted to 4.5 by addition of 3.2 g. of 50% sodium hydroxide solution. The resulting mass was stirred for 1.5 hours at 0°–5°C. and the precipitated α-L-aspartyl-L-phenylalanine methyl ester was recovered by filtration. The recovered cake was washed with five 6 ml. portions of 0°–5°C. water and then dried to yield 6.7 g. of α-L-aspartyl-L-phenylalanine methyl ester having a purity of greater than 98% (by TLC).

While the illustrative embodiments of the invention have been described hereinbefore with particularity it will be understood that various other modifications will be apparent to and can be readily made by those skilled in the art without departing from the scope and spirit of the invention. Accordingly, it is not intended that the scope of the claims appended hereto be limited to the examples and descriptions set forth herein but rather that the claims be construed as encompassing all the features of patentable novelty which reside in the present invention including all features which would be treated as equivalents thereof by those skilled in the arts to which the invention pertains.

The embodiments of this invention in which an exclusive property or privelege is claimed are defined as follows:

1. A process comprising reacting an N-protected-L-aspartic anhydride with L-phenylalanine to form N-protected-α-L-aspartyl-L-phenylalanine wherein the N-protecting group is selected from the group consisting of formyl, acetyl, benzoyl, substituted and unsubstituted carbobenzoxy, t-butoxycarbonyl and the hydrohalide salts, removing the protecting group from the N-protected-α-L-aspartyl-L-phenylalanine to form α-L-aspartyl-L-phenylalanine and esterifying the α-L-aspartyl-L-phenylalanine with an alkanol having from 1 to 3 carbon atoms to form the corresponding α-L-aspartyl-L-phenylalanine alkyl ester which is recovered.

2. A process according to claim 1 wherein the N-protected-L-aspartic anhydride is N-formly-L-aspartic anhydride.

3. A process according to claim 2 wherein the N-formyl-L-aspartic anhydride is reacted with L-phenylalanine in the presence of glacial acetic acid.

4. A process according to claim 2 wherein the formyl group is removed from N-formyl-α-L-aspartyl-L-phenylalanine by hydrolysis.

5. A process according to claim 4 wherein the hydrolysis is carried out by treating the N-formyl-α-L-aspartyl-L-phenylalanine with an aqueous solution of hydrogen chloride.

6. A process according to claim 1 wherein the esterification is conducted in the presence of hydrogen chloride.

7. A process according to claim 1 wherein the α-L-aspartyl-L-phenylalanine alkyl ester is recovered in the form of an acid salt.

8. A process according to claim 7 wherein the acid salt is hydrochloride salt.

9. A process according to claim 1 wherein the alkanol is methanol.

10. A process according to claim 9 wherein the esterification is conducted in the presence of hydrogen chloride.

11. A process according to claim 10 wherein the α-L-aspartyl-L-phenylalanine methyl ester is removed in the form of a hydrochloride salt.

12. A process comprising reacting N-formyl-aspartic anhydride with l-phenylalanine in glacial acetic acid to form N-formyl-α-L-aspartyl-L-phenylalanine, removing the formyl group from N-formyl-α-L-aspartyl-L-phenylalanine by hydrolysis with an aqueous solution of hydrogen chloride and esterifying the resulting α-L-aspartyl-L-phenylalanine with methanol in the presence of hydrogen chloride to form α-L-aspartyl-L-phenylalanine methyl ester and recovering the α-L-asparatyl-L-phenylalanine methyl ester.

13. N-protected- α-L-aspartyl-L-phenylalanine.

14. N-formyl-α-L-aspartyl-L-phenylalanine.

* * * * *

UNITED STATES PATENT OFFICE
CERTIFICATE OF CORRECTION

PATENT NO. : 3,933,781
DATED : January 20, 1976
INVENTOR(S) : Gerald L. Bachman; Marvin L. Oftedahl; and Billy D. Vineyard It is certified that error appears in the above-identified patent and that said Letters Patent are hereby corrected as shown below:

Column 1, line 2, "<" should be corrected to -- α --.

Column 2, line 64, "1,0" should be corrected to -- 1.0 --.

Column 3, line 66, "aspartyl-1-phenylalanine" should be corrected to -- aspartyl-L-phenylalanine --.

Column 4, line 28, "aspantyl" should be corrected to -- aspartyl --.

Column 5, line 68, "place" should be corrected to -- plate --.

Column 7, line 19, "[α" should be corrected to -- [α] --.

Column 10, line 16, "formly" should be corrected to -- formyl --; same column, line 44, after "formyl" and before "aspartic" there should be added -- -L --; same column, line 45, "1-phenylalanine" should be corrected to -- L-phenylalanine --.

Signed and Sealed this twenty-seventh Day of April 1976

[SEAL]

Attest:

RUTH C. MASON
Attesting Officer

C. MARSHALL DANN
Commissioner of Patents and Trademarks